United States Patent [19]
Sklar et al.

[11] Patent Number: 5,626,595
[45] Date of Patent: *May 6, 1997

[54] AUTOMATED SURGICAL INSTRUMENT

[75] Inventors: Martin J. Sklar, Needham; Ronald J. Sampson, Jr., Haverhill; Jonathan D. Schiff, Andover, all of Mass.

[73] Assignee: Automated Medical Instruments, Inc., Needham, Mass.

[*] Notice: The term of this patent shall not extend beyond the expiration date of Pat. No. 5,350,355.

[21] Appl. No.: 321,070

[22] Filed: Oct. 11, 1994

Related U.S. Application Data

[63] Continuation-in-part of Ser. No. 270,821, Jul. 5, 1994, which is a continuation of Ser. No. 837,352, Feb. 14, 1992, Pat. No. 5,350,355.

[51] Int. Cl.$^6$ .................................................. A61B 17/00
[52] U.S. Cl. ................................................. 606/170; 606/180
[58] Field of Search .................................. 606/167, 170, 606/180, 171; 128/4, 6

[56] References Cited

U.S. PATENT DOCUMENTS

| | | |
|---|---|---|
| 2,710,000 | 6/1955 | Cromer et al. . |
| 3,391,289 | 7/1968 | Danilewicz et al. . |
| 3,528,424 | 9/1970 | Ayres . |
| 3,817,251 | 6/1974 | Hasson . |
| 3,913,582 | 10/1975 | Sharon . |
| 3,926,192 | 12/1975 | Van Maren . |
| 3,945,597 | 3/1976 | Klein . |
| 4,016,881 | 4/1977 | Rioux et al. . |
| 4,143,652 | 3/1979 | Meier et al. . |
| 4,174,715 | 11/1979 | Hasson . |
| 4,342,951 | 8/1982 | Muller et al. . |

(List continued on next page.)

FOREIGN PATENT DOCUMENTS

| | | |
|---|---|---|
| 1126119 | 6/1982 | Canada . |
| 0246086 | 11/1987 | European Pat. Off. . |
| 0449663A2 | 10/1991 | European Pat. Off. . |
| 2800607 | 10/1978 | Germany . |
| 143033 | 7/1980 | Germany . |
| 1123675 | 11/1984 | U.S.S.R. . |
| 1178419 | 9/1985 | U.S.S.R. . |
| 936893 | 7/1990 | U.S.S.R. . |

OTHER PUBLICATIONS

Perry, Tony, "The Doctor is (Plugged) In", Los Angeles Times, Aug. 27, 1993.
Foreman, Judy, "Endoscopy–The Real Cutting Edge", The Boston Globe, Health/Science Section, Oct. 28, 1991, pp. 25–26.
OR Manager, "Robotic Assistant for Laparoscopic Surgery", Jan. 1994, vol. 10, No. 1.
NASA Tech Briefs, "Robotics For Safer Surgery", Jan. 1994, vol. 18, No. 1.
Product Specification Sheet, "AESOP: Automated Endoscopic System for Optimal Positioning".
Product Specification Sheet, "AESOP: Automated Endoscopic System for Optimal Positioning, Jan. 20, 1994".
Product Specification Sheet, "Enhancing Performance Through Robotics".
Product Specification Sheet, "Robotic Enhancement Technology".

*Primary Examiner*—Michael Powell Buiz
*Assistant Examiner*—William W. Lewis
*Attorney, Agent, or Firm*—Cesari and McKenna, LLP

[57] ABSTRACT

An automated surgical instrument for performing minimally-invasive surgery comprises a rigid cannula having a lumen for receiving a surgical tool at the distal end thereof. The tool can comprise a variety of linkage-operated tools, such as a grasper, clamp or scissor. The tool can also comprise an optical or gas channel. The cannula is supported on a ball-and-socket-type swivel assembly that pivots freely along orthogonal axes. The swivel is mounted on a movable arm assembly that extends and retracts. The arm assembly is mounted to a base that moves the arm assembly from side to side. Pivoting of the cannula occurs in response to movement of the arm assembly along the base and through extension and retraction of the arm.

35 Claims, 14 Drawing Sheets

U.S. PATENT DOCUMENTS

| | | |
|---|---|---|
| 4,392,485 | 7/1983 | Hiltebrandt . |
| 4,418,692 | 12/1983 | Guay . |
| 4,473,074 | 9/1984 | Vassiliadis . |
| 4,491,435 | 1/1985 | Meier . |
| 4,503,842 | 3/1985 | Takayama . |
| 4,503,854 | 3/1985 | Jako . |
| 4,517,963 | 5/1985 | Michel . |
| 4,565,423 | 1/1986 | Ueda . |
| 4,573,452 | 3/1986 | Greenberg . |
| 4,600,938 | 7/1986 | Sluyter et al. . |
| 4,600,939 | 7/1986 | Sluyter et al. . |
| 4,600,940 | 7/1986 | Sluyter . |
| 4,611,888 | 9/1986 | Prenovitz et al. . |
| 4,639,772 | 1/1987 | Sluyter et al. . |
| 4,644,950 | 2/1987 | Valli . |
| 4,644,952 | 2/1987 | Patipa et al. . |
| 4,657,018 | 4/1987 | Hakky . |
| 4,700,702 | 10/1987 | Nilsson . |
| 4,708,125 | 11/1987 | Miketi et al. . |
| 4,784,137 | 11/1988 | Kulik et al. . |
| 4,791,934 | 12/1988 | Brunnett . |
| 4,846,155 | 7/1989 | Kimura . |
| 4,858,608 | 8/1989 | McQuilkin . |
| 4,863,133 | 9/1989 | Bonnell . |
| 4,905,668 | 3/1990 | Ohsawa . |
| 4,941,454 | 7/1990 | Wood et al. . |
| 4,944,738 | 7/1990 | Rodriguez . |
| 4,944,741 | 7/1990 | Hasson . |
| 4,959,710 | 9/1990 | Uehara et al. . |
| 4,977,886 | 12/1990 | Takehana et al. . |
| 4,982,725 | 1/1991 | Hibino et al. . |
| 5,002,557 | 3/1991 | Hasson . |
| 5,018,509 | 5/1991 | Suzuki et al. . |
| 5,019,121 | 5/1991 | Krauter . |
| 5,020,535 | 6/1991 | Parker et al. . |
| 5,026,387 | 6/1991 | Thomas . |
| 5,184,601 | 2/1993 | Putnam . |
| 5,350,355 | 9/1994 | Sklar . |

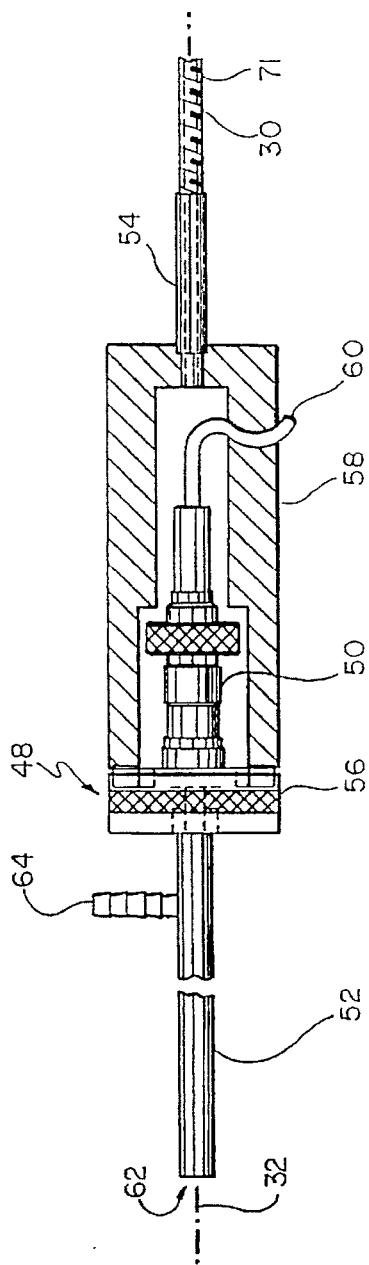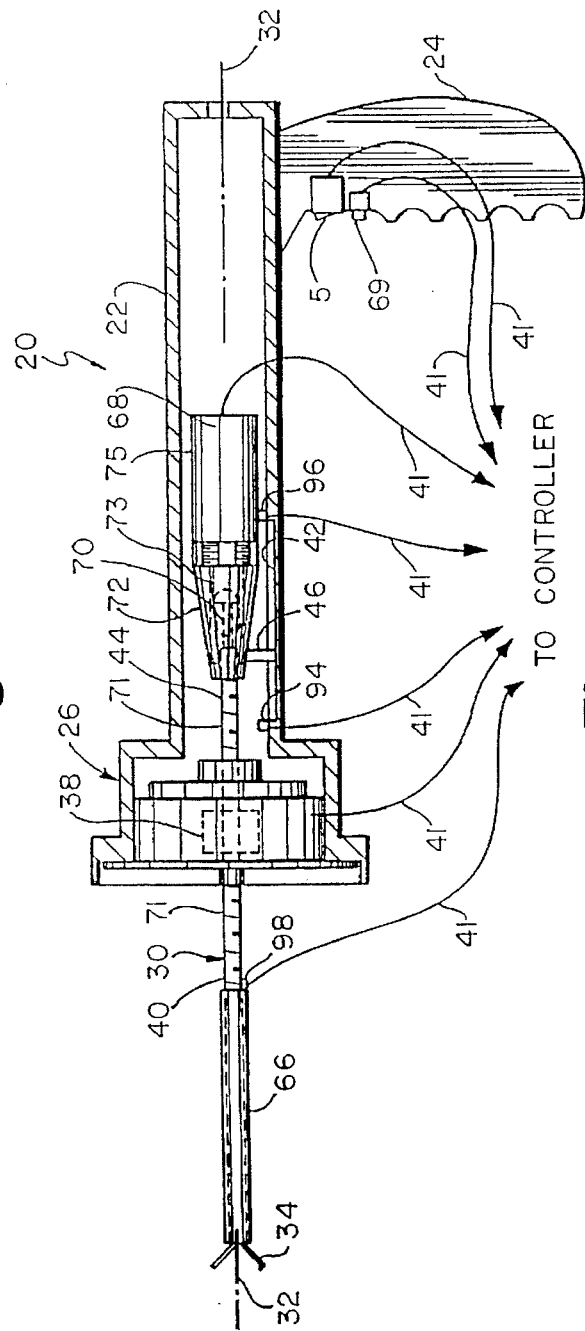

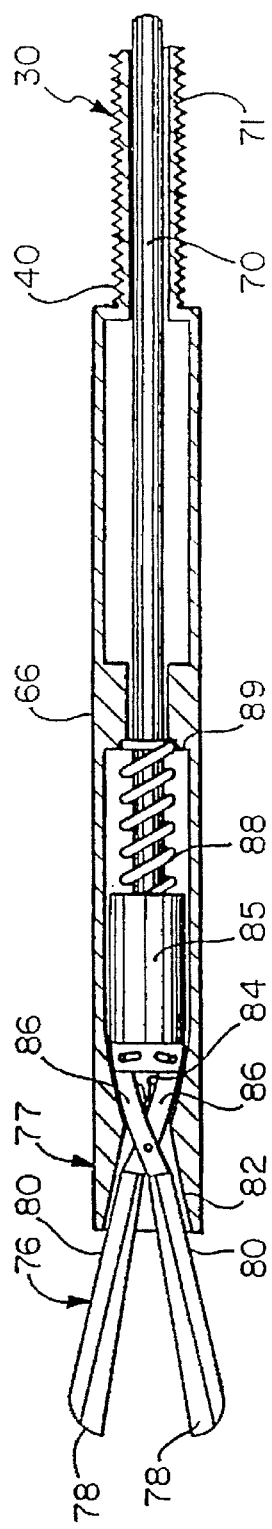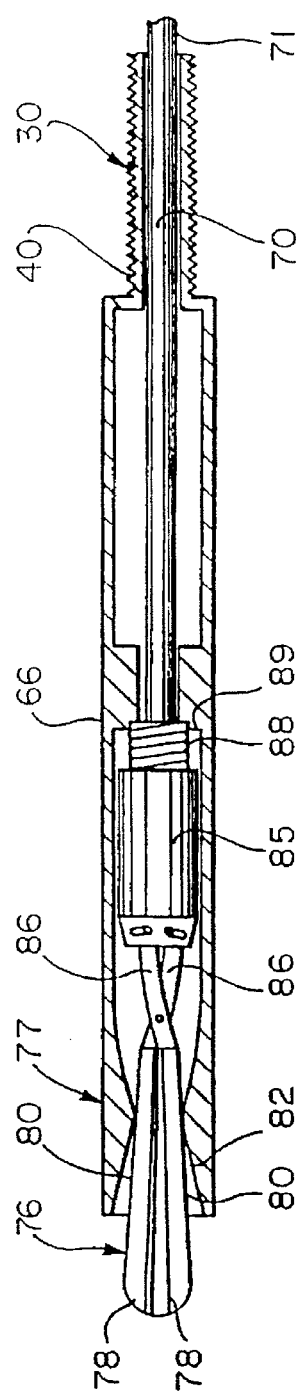
Fig. 5a
Fig. 5b

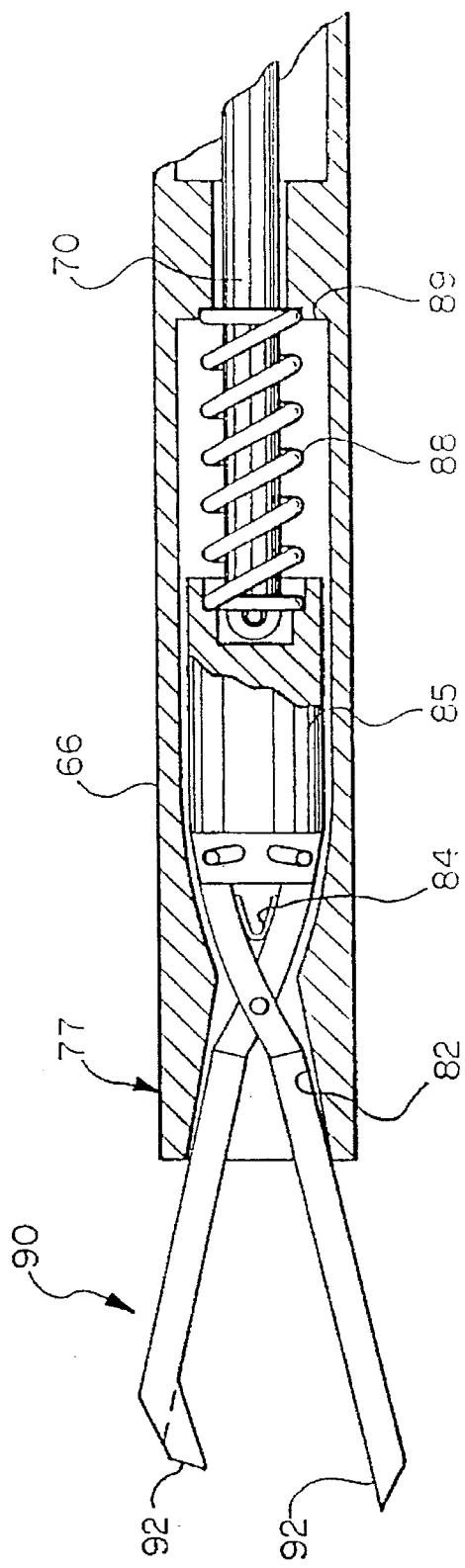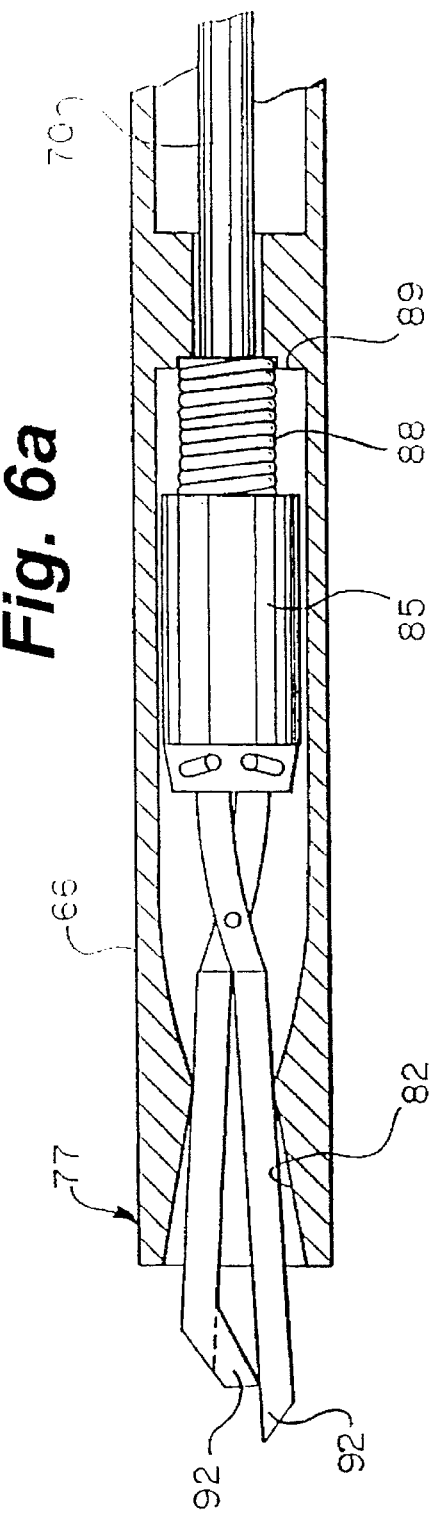

AUTOMATED SURGICAL INSTRUMENT

RELATED APPLICATION

This application is a continuation-in-part of copending U.S. patent application Ser. No. 08/270,821, filed Jul. 5, 1994, which is a continuation of U.S. patent application Ser. No. 07/837,352, filed Feb. 14, 1992, now U.S. Pat. No. 5,350,355.

FIELD OF THE INVENTION

This invention relates to an automated surgical instrument and a system for performing minimally-invasive surgical procedures with such instruments.

BACKGROUND OF THE INVENTION

In recent years, the use of laparoscopic instruments to perform minimally-invasive surgical procedures has become increasingly popular. In such procedures, a device termed a laparoscope, having an elongated substantially tubular member is inserted into the body of the patient through a relatively small incision in the skin. The distal end tube or "cannula" is positioned proximate an area inside the body upon which a surgical procedure is required. The distal end generally includes a lens and, typically, a light source to illuminate the interior of the body. The lens transmits received images from inside the body to a camera located, generally, outside of the body near a proximal end of the cannula. The camera may be interconnected to a video monitor so that a surgeon may view the operation area. Hence, the surgeon may view an interior portion of the body without the need of a large incision to open an area to external viewing.

Several additional laparoscopic instruments, also having elongated tubular cannuli, may be inserted through additional incisions in the skin to positions adjacent the laparoscope's distal end. These instruments may include a number of surgical tools including scissors, graspers and retractors capable of mechanical movement to perform desired surgical operations upon the area. The laparoscope allows the surgeon to view the progress of the instruments and, hence, guide the other laparoscopic instruments to perform the operation.

Conventional surgical procedures in which the surgeon performs the operation through an open incision, using hand tools such as scalpels and forceps, generally inflict significantly more trauma upon the patient and entail a more lengthy recovery time than for the relatively minor incisions necessitated by laparoscopic instruments. Thus, for many types of surgery, the use of laparoscopic instruments is largely preferred.

A disadvantage to the use of laparoscopic instruments, however, has been the need for a substantial number of operators in order to effectively employ the procedure. To date, most Laparoscopes and laparoscopic instruments have been designed strictly for hand-held manual operation. Some laparoscopes have utilized supports to aid in holding them stationarily, but insertion, retraction and readjustment of the cannula has been performed manually. Each instrument usually must be operated by a single staff member and that staff member must maintain the instrument in a proper location throughout the procedure by manually readjusting it as needed. For example, the camera may require frequent refocusing and redirecting. In addition, instruments having tools that require manipulation must be operated by the user while the user simultaneously holds the laparoscope at an appropriate location which can tax the coordination of the user and quickly fatigue him or her.

The continual manipulation of instruments by hand, therefore, can seriously impede the efficiency of an operating staff, particularly during a long and difficult procedure.

In view of the disadvantages associated with the use of manually operated laparoscopic instruments, this invention has, as one object to provide a laparoscopic instrument that may be operated remotely by the user. This invention also enables more accurate and stable movement of laparoscopic tools relative to an area of operation and allows manipulation of a greater number of laparoscopic instruments by fewer users than manually-operated laparoscopic instruments. This invention also reduces operating staff fatigue by automating more of the control and movement functions necessary in laparoscopic surgery.

SUMMARY OF THE INVENTION

The disadvantages of the prior art are overcome according to this invention by providing an automated surgical instrument that is adapted to mechanically drive a cannula toward and away from a stationary housing. The housing can be adapted to be held by a hand or can, otherwise, be adapted for mounting on a stationary or movable support. The user manipulates a switch or other control to power a linear motor within the housing that drives a cannula to place its distal end at a predetermined distance from the housing. As such, the cannula may be brought to a certain point within the body through an incision and subsequently driven to an appropriate area upon which an operation is to occur.

A variety of automated tools can be attached to the cannula. These tools include scissors, graspers, trocars, retractors, and electrocautery devices. The cannula can also carry a laparoscope having a camera mount for viewing an operation area. Actuators within the housing are linked to the tools at the distal end of the cannula by means of linkages passing through a lumen in the cannula. Switches for operating the actuators can be located similarly to those for operating the linear drive motors, such as upon the housing, on an associated handle or on a remote control.

According to an alternate embodiment, this invention provides, an automated surgical instrument for performing minimally-invasive surgery comprises a rigid cannula having a lumen for receiving a tool at the distal end thereof. The tool can comprise a variety of linkage-operated tool, such as a grasper, clamp or scissor. The tool can also comprise an optical or gas channel. The cannula is supported on a ball-and-socket-type swivel assembly that pivots freely along orthogonal axes. The swivel is mounted on a movable arm assembly that extends and retracts. The arm assembly is mounted to a base that moves the arm assembly from side to side. Pivoting of the cannula occurs in response to movement of the arm assembly along the base and through extension and retraction.

BRIEF DESCRIPTION OF THE DRAWINGS

The foregoing and other objects and advantages of the invention will become more clear with reference to the following detailed description of the preferred embodiments as illustrated by the drawings in which:

FIG. 3 is a more-detailed side cross-section of the laparoscope and camera of FIG. 2;

FIG. 4 is a somewhat schematic side cross-section of the automated surgical instrument of FIG. 1 including a tool and actuating mechanism according to this invention;

FIGS. 5(a) and 5(b) are side cross-sections of a surgical scissor for use with the automated surgical instrument of FIG. 4 in opened and closed positions, respectively;

FIGS. 6(a) and 6(b) are side cross-sections of a grasping tool for use with the automated surgical instrument of FIG. 4 in opened and closed positions respectively;

DETAILED DESCRIPTION OF THE PREFERRED EMBODIMENT

Figure 1:
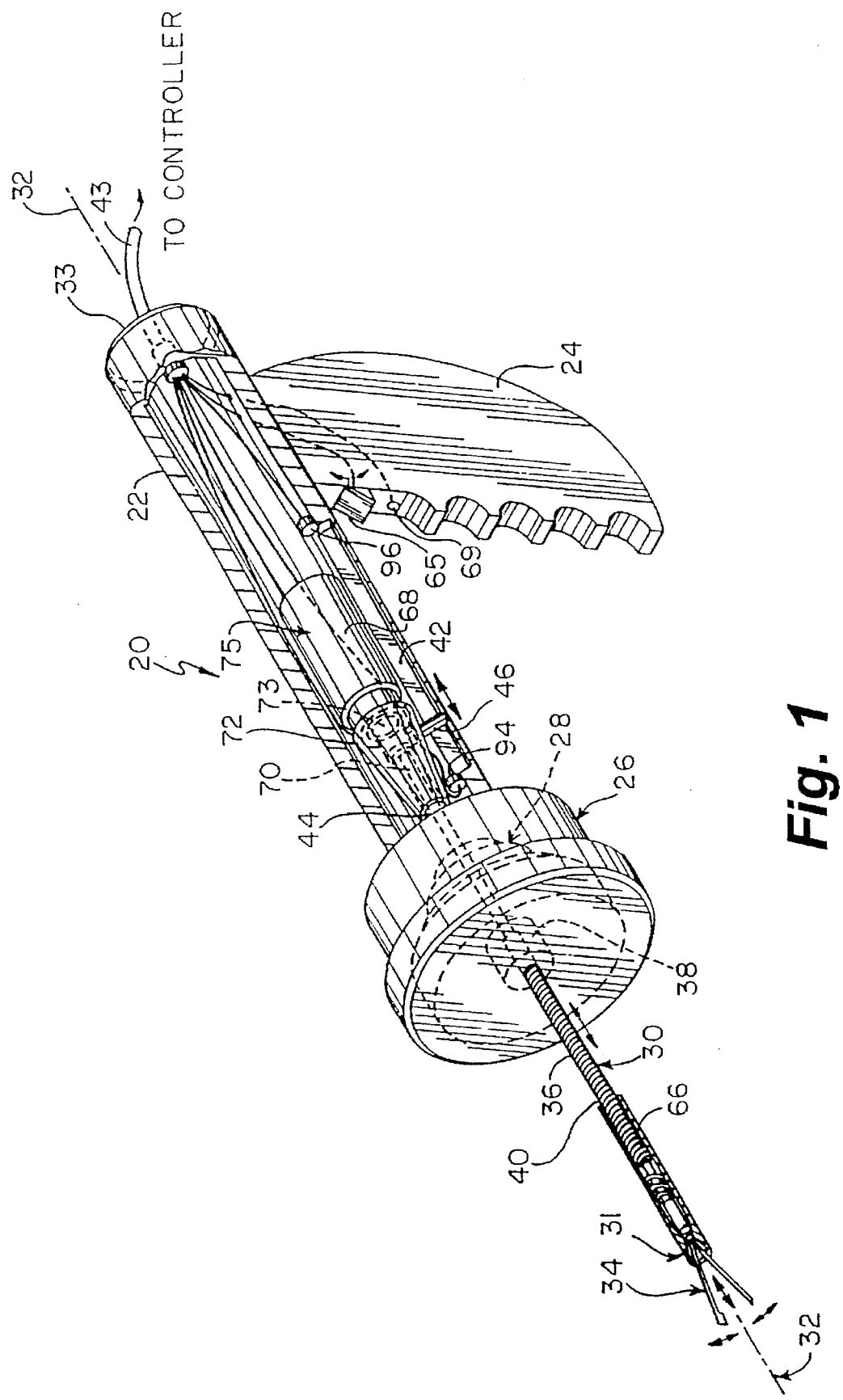
FIG. 1 is an exposed isometric view of an automated surgical instrument according to this invention.

FIG. 1 is an overview of an automated surgical instrument 20 according to this invention. The instrument 20 comprises a housing 22 of plastic, metal or other suitable materials. The housing in this embodiment is substantially cylindrical and elongated. This shape facilitates its mounting in a suitable support or, alternatively, allows it to be held by a grasping hand for manual directing. An optional secondary handle 24 may be attached to the narrowed proximal end of the housing 22 for increased control where manual manipulation or directing is desired. The more distal end of the housing includes an enlarged diameter section 26. The enlarged section 26 houses a linear drive motor 28 for driving an elongated cannula 30 according to this invention. As used herein, "distal" shall mean toward the free end 31 of the cannula 30 and "proximal" shall mean toward the rear end 33 of the housing 22.

The cannula 30 in this embodiment is substantially rigid and structured as a hollow tube having an outer diameter of between 0.2 and 0.4 inches and an inner luminal diameter of between 0.1 and 0.3 inches. The linear drive motor 28 allows the cannula 30 to move relative to its longitudinal axis (the axis in the elongated direction) 32 toward and away from the housing 22. In one embodiment approximately six inches of linear extension of the cannula 30 is contemplated. However, the extension distance of the cannula 30 can be adapted as necessary to perform a particular task. As used herein, the term "cannula" shall refer generally to the elongated tubular portion moves relative to the instrument housing 22.

Figure 2:
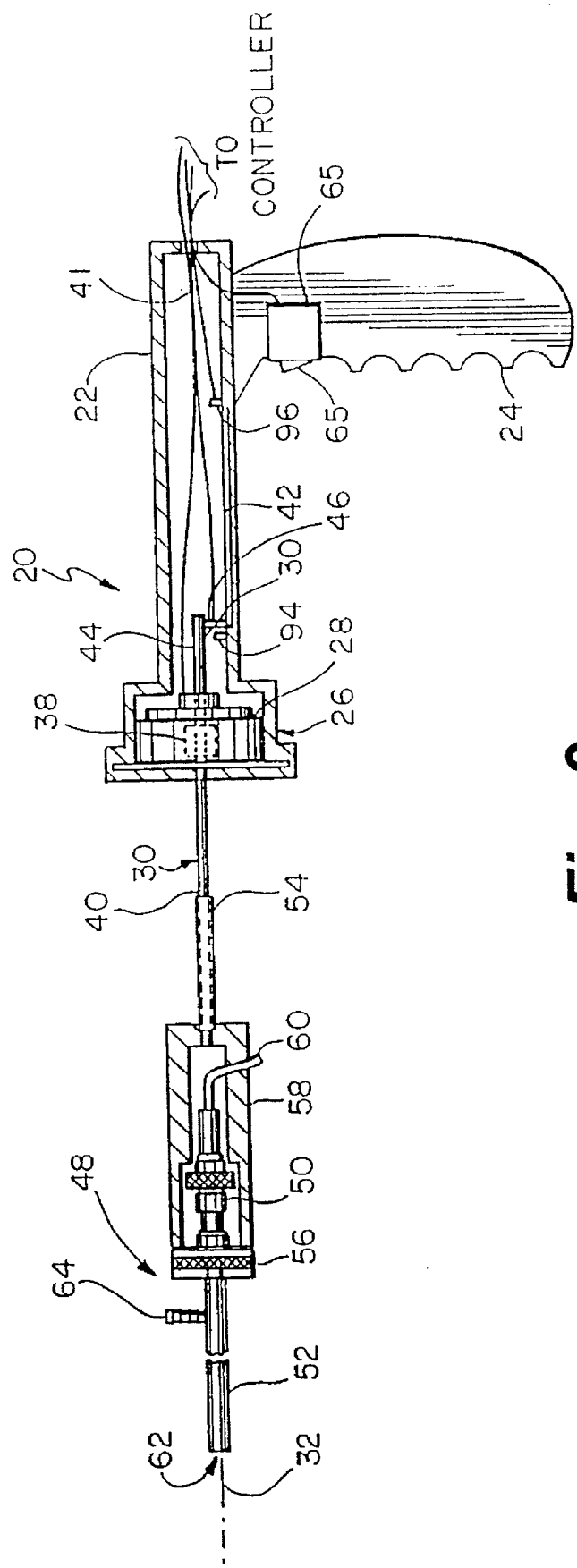
FIG. 2 is a somewhat schematic side cross-section of the automated surgical instrument of FIG. 1 including a laparoscope with a mounted camera according to this invention.

The cannula 30 is adapted to include a tool 34 at its distal end. The illustrated tool 34 is a pincer-like grasper. Tools will be described further below but, generally, may include a variety of mechanical surgical tools such as scissors and graspers or optical tools such as a laparoscope. FIGS. 2–3 particularly show a laparoscope positioned at the end of the instrument 20 for viewing the interior of a body.

According to this embodiment, the linear drive motor 28 comprises a screw drive. The cannula 30, thus, includes a threaded surface 36 that engages a rotating threaded nut 38 in the motor 28. The motor 28 rotates in each of opposite directions to, respectively, retract and extend the cannula 30. The nut 38 is coaxially positioned within the motor 28 and the cannula 30 can pass through the motor 28 and nut 38 into and out of the housing 22. In this manner, the distal end 40 of the cannula 30 may be accurately positioned relative to the housing 22. To facilitate accurate positioning, the linear motor 28 according to this invention comprises a position-controllable motor such as a stepper motor or a servo motor. Electrical components such as the linear drive motor 28 as used herein are operated by a conventional analog or digital controller (not shown) that receives control inputs from various switches and sensors, both on and remote from the housing 22. The control inputs are translated by the controller into electrical signals to operate the components in a manner to be described further below. Electrical signals in this embodiment are carried through lead wires 41 that can be joined into a control cable 43 exiting the rear 33 of the housing 22 as shown.

The cannula 30 (or an attached proximally positioned member of the cannula) is affixed to a housing channel 42 adjacent the cannula's proximal end 44 by means of a locking pin 46. The pin 46 and channel 42 are sized and arranged so that the cannula 30 may move along the housing 22 in a direction of its longitudinal axis 32, but is prevented from rotating relative to the housing 22 by engagement of the pin 46 with the side walls of the channel 42. In this manner, the cannula 30 does not rotate with the nut 38. Rather, rotation of the nut 38 is translated into linear motion of the cannula 30 along its longitudinal axis 32.

While a screw drive mechanism is depicted, according to a preferred embodiment of this invention, for moving the cannula 30, a variety of other types of linear motors may be utilized to provide extension and retraction of the cannula 30 relative to the housing 22. For example, an electromagnetic linear motor can be utilized to move a magnetically attractive cannula. Similarly, a pneumatic or hydraulic linear actuator can be utilized or a rack and pinion system in which the cannula comprises a rack driven by a set of rotating gears within the motor can be provided.

The instrument 20 according to this invention is designed to carry a variety of accessories upon the distal end 40 of its cannula 30. These accessories are adapted to be inserted through an incision in a patient while the housing 22 and the motor driven (threaded) portion of the cannula 30 remain positioned externally of the patient. FIGS. 2–6 detail variously possible applications of the surgical instrument 20 according to this invention.

FIGS. 2–3 illustrate, in detail, the use of a laparoscope 48 having a camera 50 directed toward its distal end 52 in the surgical instrument 20 according to this invention. The laparoscope 48 is attached by means of a sleeve 54 to the distal end 40 of the lead screw driven cannula 30. The sleeve 54 supports a camera mount 56 that is enclosed in a housing 58 according to this embodiment. The camera 50 includes a lead 60 that projects from the housing 58 and may interconnect with a display device at a remote location (see generally FIG. 7). The distal end 52 of the laparoscope 48 is adapted to be positioned through an incision in the patient to view an area facing the tip 62 of the distal end. Note that the distal end 52 can include a gas port 64 for injecting an inert gas into the cavity of the patient. This allows inflation (or "insufflation") of the affected area for better viewing. The laparoscope 48 can be supported by an external device such as an articulating arm (see generally FIG. 7) or can be hand held.

A secondary handle 24 is provided for gripping and control. This handle is optional, however, and controls can be positioned on the housing or at a remote location. The handle 24 includes a switch 65 having two poles enabling both extension and retraction of the lead screw driven cannula 30. Thus, a surgeon can locate the distal end 62 of the laparoscope 48 within a patient and then finely adjust the positioning of the distal end 62 by moving the lead screw driven cannula 30. The positioning of the distal end 62 in the patient can be quickly altered following an initial insertion by simply toggling the switch 65 to obtain the desired positioning of the distal end 52 of the laparoscope 48.

As noted above, a variety of additional laparoscopic surgical tools can be provided at the distal end 40 of the lead screw driven cannula 30 according to this invention. Referring again to FIG. 1 and now also to FIG. 4, an embodiment of the surgical instrument 20 of this invention adapted to actuate a mechanical laparoscopic surgical tool 34 is shown. The tool 34 is mounted in a sleeve 66 adapted for insertion through an incision. The tool 34 in this example is a form of grasping device that opens and closes upon actuation by the user.

Actuation of the grasper tool 34 is accomplished by means of an electrically powered linear solenoid actuator 68 positioned within the housing 22 at the proximal end 44 of the lead screw driven cannula 30. The solenoid 68 actuates a linkage 70 that transfers force to operate the tool 34. In this embodiment, the solenoid actuator 68 is fixedly joined to the proximal end 44 of the cannula 30 by a conical sleeve 72 and the linkage 70 passes through the lumen 71 of the cannula 30. A switch 69 on the handle 24 operates the solenoid 68 to move it in a proximally directed direction. The linkage 70 can comprise a tensioned cable or a rigid rod. The conical sleeve 72 of the actuator 68 and the proximal end 44 of the cannula support the locking pin 46 that engages the housing channel 42 to prevent the cannula 30 and actuator 68 from rotating as the drive nut 38 rotates. Both the cannula 30 and the sleeve 66 include the lumen 71 along their respective portion of the longitudinal axis 32 that allows the linkage 70 to pass from the actuator 68 to the tool The solenoid actuator 68 includes a core 73 capable of movement along the longitudinal axis 32 freely relative to the solenoid outer housing 75. The housing 75 is fixed to the conical sleeve 72 and, hence to the cannula 30. This configuration allows the linkage 70 to move longitudinally while the cannula 30 remains stationary. The operation of some typical tools will now be described below.

FIGS. 5(a) and 5(b) show a scissor tool 76 positioned within the sleeve 66 at the distal end 77 of the sleeve 66. The scissor 76 includes a pair of sharp blades 78 that, in an open position (FIG. 5(a)), project from the distal end 75 of the sleeve 66. The outer edges 80 of the scissor blades 78 abut a frustoconical inner portion 82 of the sleeve distal end 77. The solenoid actuator 68, when powered, moves the linkage 70 proximally. As the linkage 70 pulls on a block 85 holding the proximal scissor jaws 86, it draws the scissor blades 78 proximally into the sleeve 66. The blades 78 are drawn together as they move proximally by the engagement of the outer edges 80 with the narrowing walls of the frustoconical portion 82. The proximal movement of the blades 78 is opposed by the biasing force of a leaf spring 84 in the proximal jaws 86 and a coil spring 88 between the block 85 and a distal sleeve shoulder 89. The oppositely directed pulling action of the linkage 70, thus, causes the scissor blades 66 to close together as shown in FIG. 5(b).

When the actuator 68 is subsequently depowered, following a cutting stroke, the linkage 70 is free to extend distally under the biasing force of the coil spring 88 and the jaw leaf spring 84, thus allowing the scissor blades 78 to again open for the next cut.

FIGS. 6(a) and 6(b) show a similar mechanism to that described in FIGS. 5(a) and 5(b) for operating a grasper 90 according to this invention. In an opened position as shown in FIG. 6(a), the grasper arms 92 are fully extended from the distal end 77 of the sleeve 66. In a closed, grasping, position, the grasper arms 92 are almost fully retracted into the sleeve 66 with the arms 92 engaging one another and with the coil spring 88 fully compressed.

Various other laparoscopic surgical tools can be attached to the cannula 30 according to this invention. Several of these tools can utilize the solenoid actuator 68 as shown in their operation. Specific examples of surgical tools for use with the instrument 20 include, but are not limited to, trocars, clamps, staplers, retractors, electrocautery devices, vacuum retractors, needles and probes. Other mechanically actuated surgical tools are also contemplated according to this invention. Vacuum, gas and fluid can also be channeled through the lumen 71 of the cannula 30 from the housing 22 or from another location. Similarly, electrocautery wires can be routed through the lumen 71 and used with a specifically designed electrocautery tool or the wires can be incorporated into another laparoscopic surgical tool such as a grasper. The lumen 71 and any tool can also be sized and arranged to allow passage of a fiberoptic or similar optical waveguide for viewing areas adjacent the sleeve's distal end 77. These fiberoptic devices can be mounted in conjunction with one of the above-described tools.

It is contemplated according to this embodiment to control the linear drive motor 28 using a bipolar switch or controller such as a joy stick or toggle switch. The switch can be mounted upon an auxiliary handle as shown in FIGS. 1–2 and 4 (switch 65). Alternatively, the switch can be mounted upon the housing itself and/or at a remote location using, for example, a control box/display console 79 or a foot pedal 83 such as those depicted in FIG. 7.

To further prevent injury to the patient and damage to the instrument, the housing 22 and cannula 30 can be provided with a variety of safety features. FIGS. 1–2 and 4 illustrate a pair of limit switches 94 and 96 that can comprise conventional microswitches according to this embodiment. Each switch 94, 96 is positioned at a location corresponding to one of the two extremes of motion of the cannula 30 relative to the housing. The distally located switch 94 is actuated by the locking pin 46 upon extreme distal extension of the cannula 30 while the proximally located switch 96 is actuated by the pin 46 upon extreme proximal retraction of the cannula 30. Each switch 94 and 96 is interconnected with the controller or control loop (not shown) that operates to disconnect the linear drive motor 28 from its power source when one of the above-described extreme positions relative to the housing 22 is reached by the moving cannula 30. In this manner, the linear drive motor 28 is prevented from over extending the cannula 30 and causing damage to it or to the motor 28 itself. Each switch 94 and 96 only disconnects power directed in the direction of extreme positioning. In other words, once a given limit switch 94 or 96 is tripped, it is still possible to reverse the direction of travel of the cannula 30 to back the cannula 30 away from the extreme and the associated limit switch. When the cannula 30 reaches the opposing limit switch, that switch is then tripped cutting off further power to the linear motor in that direction.

The limit switches 94 and 96 according to this embodiment are particularly adapted to prevent damage to the instrument 20. Additional sensors can also be provided to the cannula 30 or a component connected with the cannula in order to prevent the exertion of undue force upon the patient's internal tissue by the driven cannula 30. FIG. 4 further illustrates a force sensor 98 positioned proximate the sleeve 66 of the surgical tool 34. Other locations along the cannula for the sensor may be utilized according to this invention. The force sensor 98 can comprise a strain gauge, pressure transducer, or a similar device for sensing small increases in the surface strain associated with increased force upon the cannula. The sensor 98 and associated circuitry are calibrated to sense a force in excess of a predetermined value. This value can be set to equal a maximum force that internal tissue can experience without damage. In this manner, the drive motor 28 will stop further advance of the cannula 30 when it begins to bind upon tissue as it is driven into the body. This ensures that the surgeon will not damage internal tissue with the distal end of the tool or laparoscope during extension. Of course, a maximum force adjustment control may be provided to change the maximum force threshold to account for differing operational requirements.

Other forms of proximity sensors may also be provided to the cannula 30 or related components in order to prevent tissue damage. Such sensors can include electrostatic and optical sensors that alert the user that the distal end of the tool or laparoscope has reached a predetermined proximity to tissue. Note that sensor signals can be transferred through the lumen by wires or fiber optic cables from these sensors to the controller (not shown). The sensors can also disable the linear drive motor 28 when the predetermined proximity is reached by the cannula 30.

As an additional feature, the instrument can also include a master power switch located on the handle or at a remote location such as a foot pedal, that allows the user to disable operation of the instrument in the event of a sudden emergency.

A plurality of surgical instruments according to this invention can be utilized and controlled simultaneously during an operative procedure. One such an arrangement is shown generally in FIG. 7. Each instrument (I-IV) is supported by a corresponding articulating arm structure 100 that includes horizontally and vertically oriented pivots 102 and 104, respectively, to allow the instrument to be moved in three dimensions. The arms 100 may be mounted to a post, the ceiling or a comparable support structure 106. The arms include a counter weight or counter force device upon each joint that allow the respective arm to remain fixed in a predetermined spatial position. By predetermined spatial position, it is meant a position suspended relative to an operating area 99 in which the distal end of the cannula may be placed at the area to be operated upon.

Figure 7:
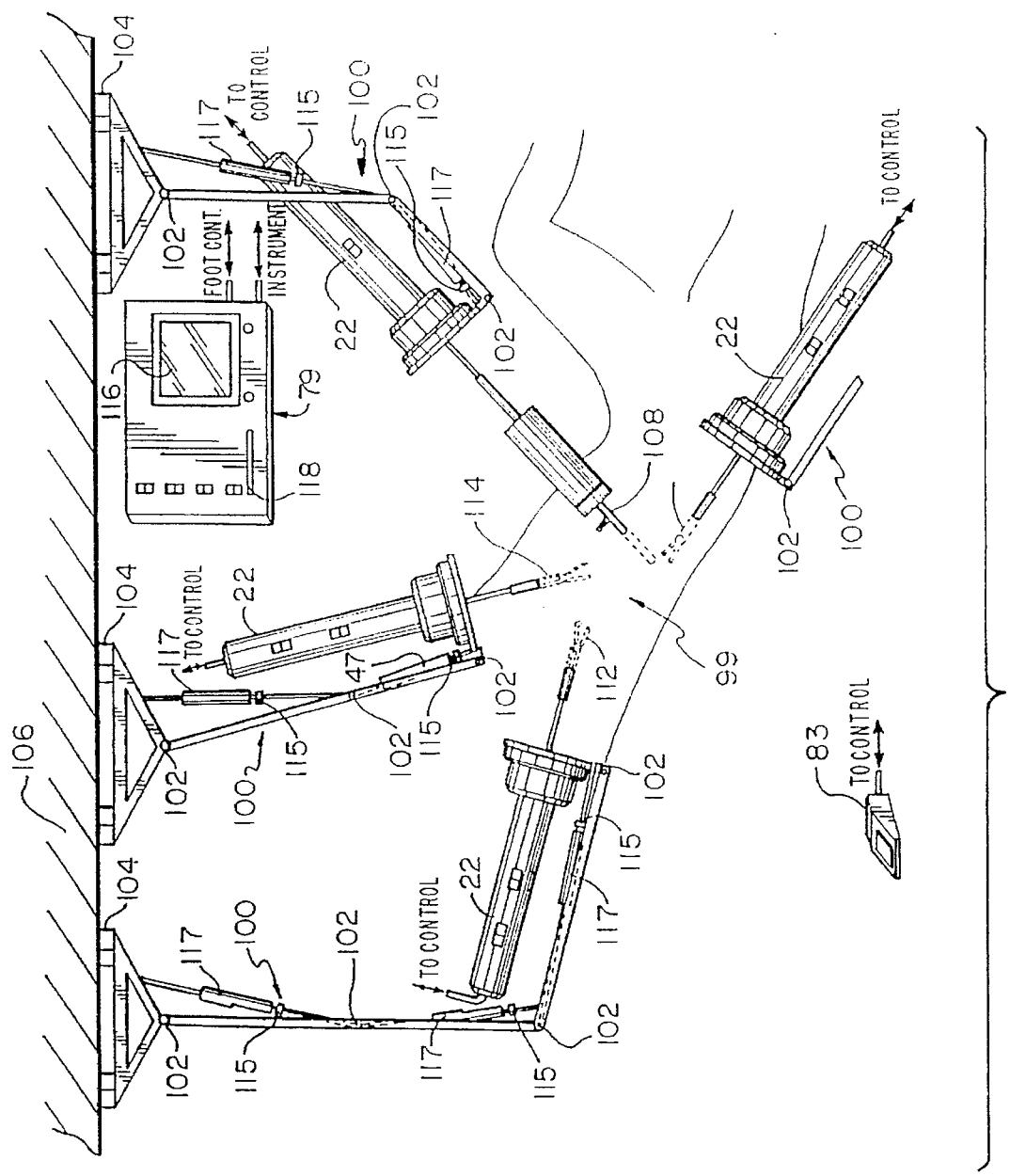
FIG. 7 is a somewhat schematic perspective view of a surgical system utilizing a plurality of automated surgical instruments according to this invention.

The arms are each stabilized by counterweighting devices which counteract the weight of the instruments to allow them to remain suspended in whatever position in which the surgeon places them. In this embodiment, the arm is stabilized by air pistons 117 located on arm sections between each horizontal pivot 102. Each arm 100 includes a locking system (lock nuts 115 on the pistons 117 in this embodiment) that allows the arm to be fixed in its desired spatial position. In the configuration of FIG. 7, four separate instruments I-IV, each having a different tool, is utilized including a laparoscope 108, a grasper 110, a scissor 112 and an electrocautery wire/pincer 114.

In air operation using the above-described system, a surgeon first forms an incision at a desired location upon the body and then lowers an instrument into a position with the distal end of its cannula positioned near or within the incision. The arm is then locked in place once the instrument cannula is aligned and angled so that it may pass through the incision into the area to be operated upon. The instrument is then powered to drive the cannula with an appropriate tool at its distal end to the area. Laparoscopic surgical tools are activated as needed to perform, for example, cutting or grasping operations. Tools are extended and retracted as the operation progresses. The laparoscope I is usually inserted first through its own incision to allow viewing, via a display 116, of the progress of the other laparoscopic instruments II-IV, which each enter the operation area 99 through, generally, their own incision.

As noted above, each instrument is operated either by switches located upon the housing or on an associated secondary handle, or upon a remote control/display console 79. Any combination of control locations can be simultaneously used during operation. In this embodiment, the console 79 acts both as a display for the laparoscope I and as a control for each of the laparoscopic instruments II-IV. Each instrument can be controlled separately by accessing the appropriate channel by means of a selector 118 on the console 79. Similarly, a foot control 83 is interconnected with the remote control console to provide optional control capability to the user. The foot control 83 could act to actuate certain selected instruments or could be utilized as an emergency power shut-off switch if necessary. Controls are also provided on the housings 22 of each instrument in this embodiment.

A system utilizing mechanized or automated laparoscopic instruments according to this invention allows for greater control and more reliable adjustment of each of the instruments employed. The automated control of each instrument allows for quicker realignment of its location within the body and more accurate and steady movement from one point to another. Devices may be held in place more steadily. Tool operations, such as cutting and grasping, also prove more predictable and accurate and fatigue of staff members is reduced. The number of required staff members is also reduced.

Figure 8:
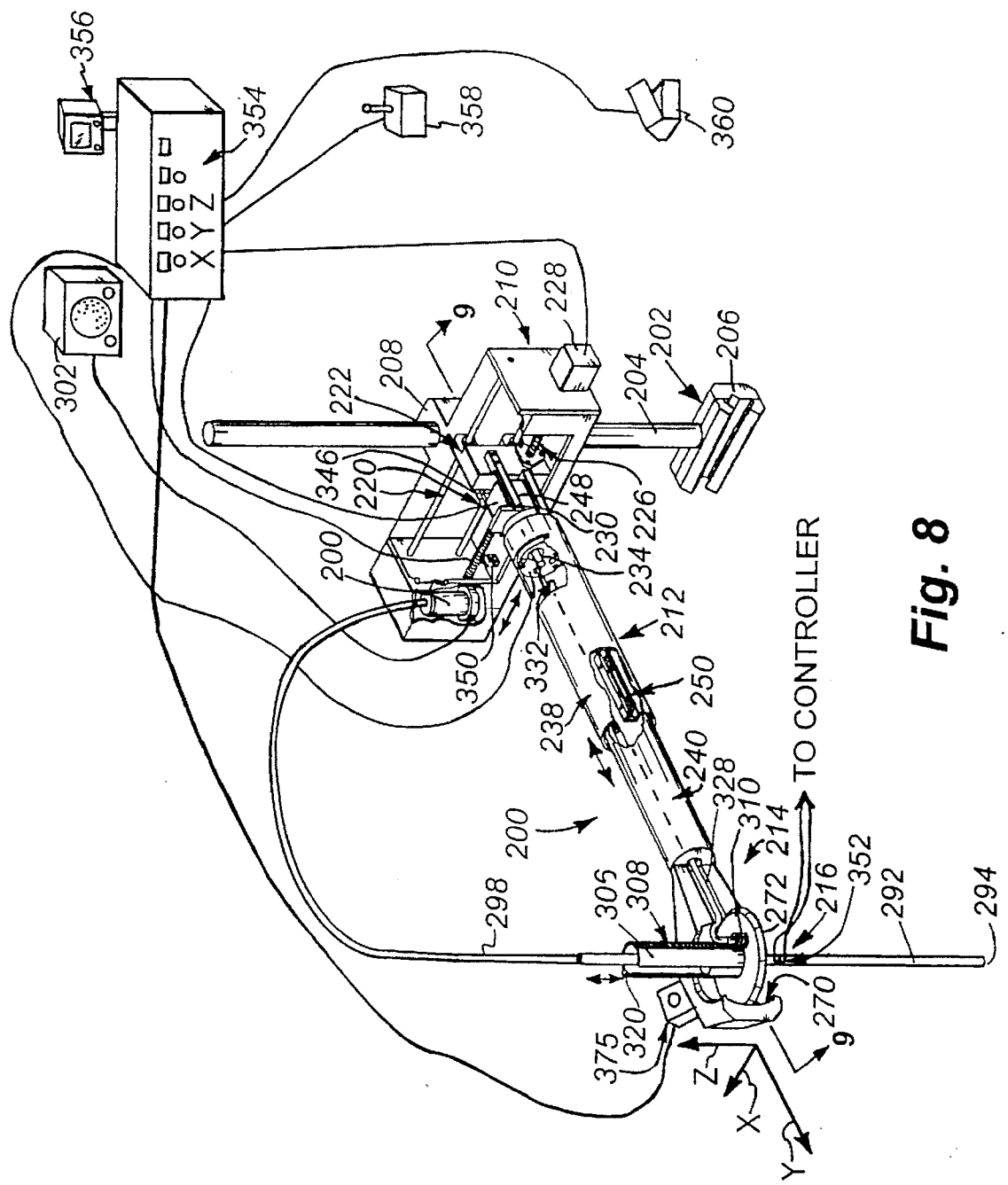
FIG. 8 is a partially-exposed isometric view of another embodiment of an automated surgical instrument according to this invention.
Figure 8A:
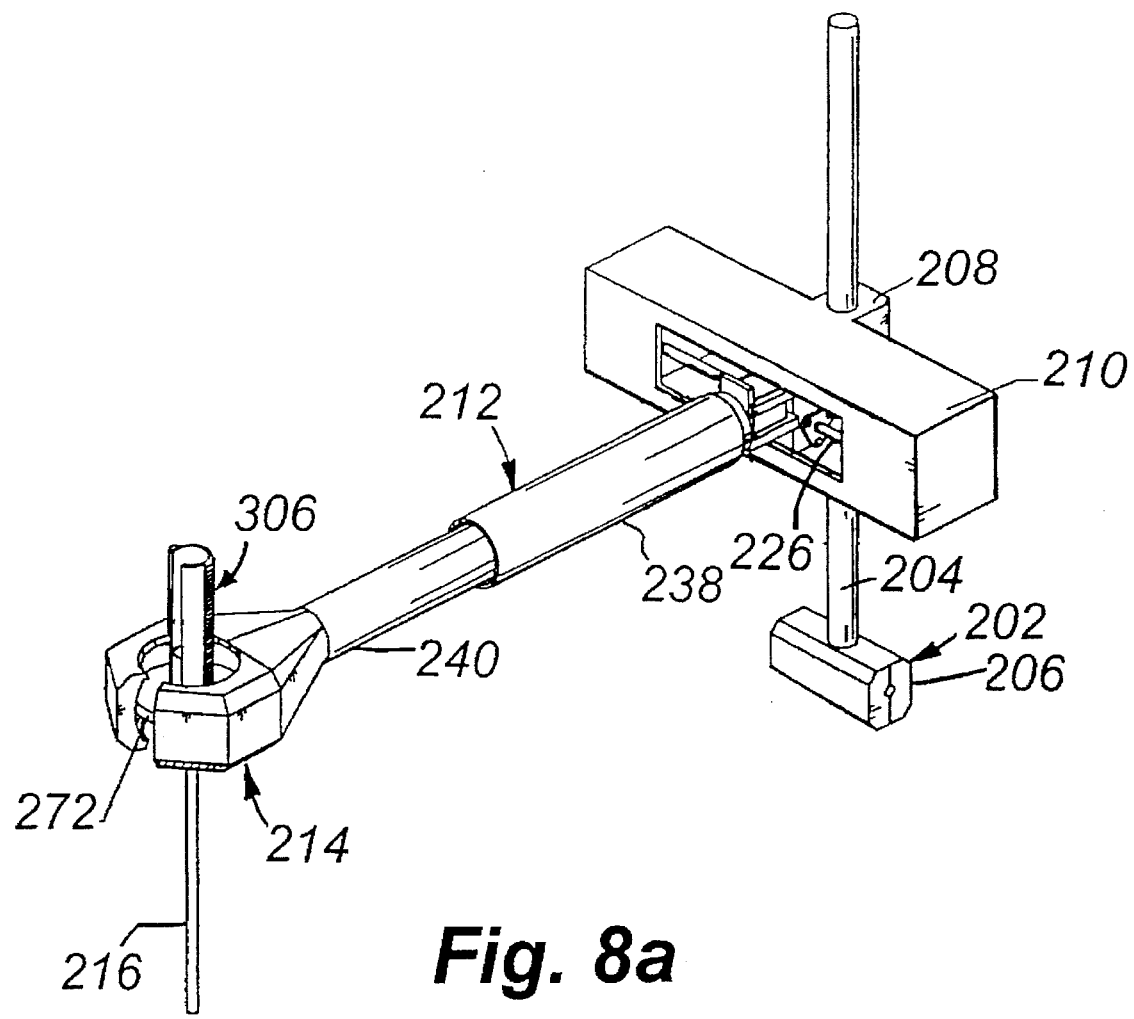
FIG. 8(a) is an isometric view of the assembled automated surgical instrument of FIG. 8.
Figure 9:
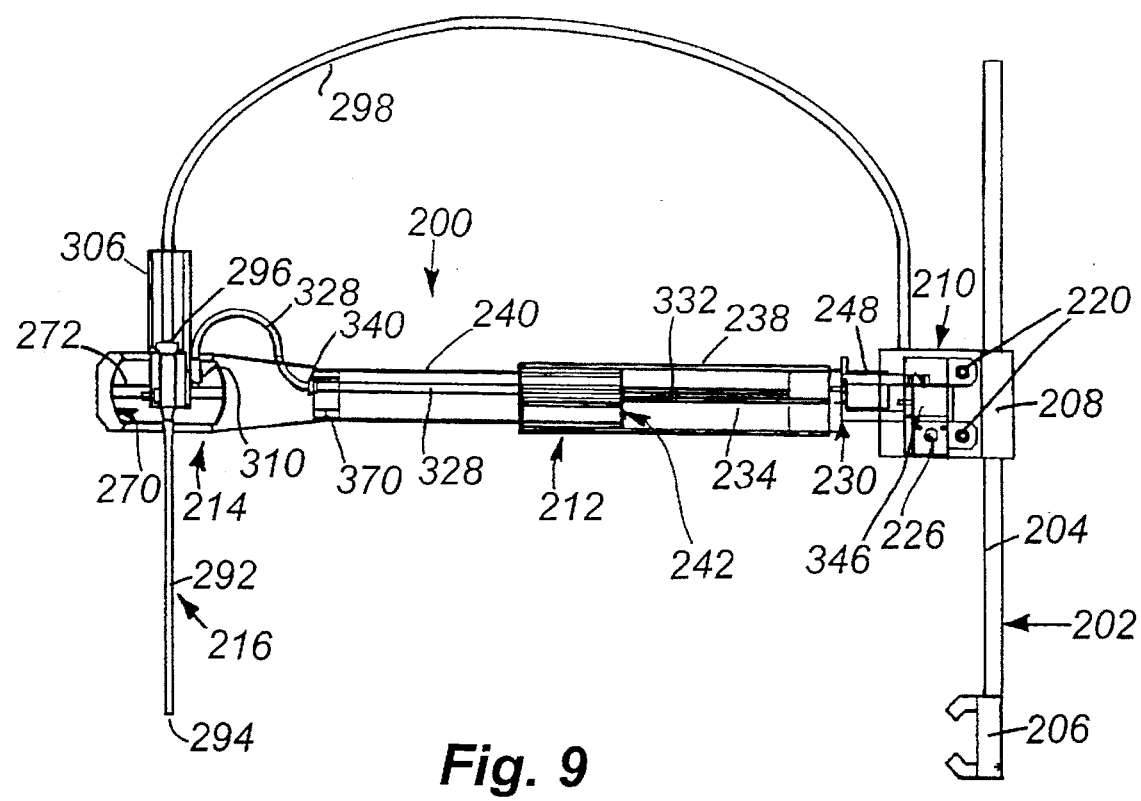
FIG. 9 is a cross section of the automated surgical instrument taken along Line 9—9 of FIG. 8.

An automated surgical instrument according to another embodiment of this invention is depicted, in overview, in FIGS. 8, 8(a) and 9. This embodiment incorporates many of the functions of an articulating arm with a laparoscope drive that operates similarly to that described in the previous embodiment. This embodiment provides the operator with additional versatility. The instrument 200 comprises a substantially-integral unit that includes a mounting base 202 having an upstanding mounting rod 204 and a table rail clamp 206. This instrument can, thus, be mounted directly on an operating table or gurney along the side of the table, or on a table rail. It is expressly contemplated that other bases can be utilized including floor mount and ceiling mount bases.

The instrument 200 is supported on the upright rod 204 by a lug 208 that can include a turn screw (not shown) or any other suitable structure for locking the lug 208 to the rod 204. Such locking should prevent both linear movement along the elongated (2) axis of the rod 204 and also rotational movement about the elongated (2) axis of the rod. The lug 208 can be moved along the rod 204 to change the elevation of the instrument 200. The lug 208 defines a projection extending from the base housing 210. The base housing shall also be denoted as the "X-drive housing" since, as described further below, this housing 210 encloses the drive that enables the instrument to be relocated along a side-to-side "X-axis". The X, Y and Z-axes, as defined herein, are illustrated in FIG. 8. Extending outwardly from the X-drive housing 210, along the "Y-axis", is a telescoping arm 212. At the distal end of the telescoping arm 212 is located a hand assembly 214. The hand assembly 214 supports the laparoscopic instrument 216 according to this embodiment. The instrument 216 can comprise a driven instrument with a rigid cannula having a form substantially similar to that shown and described with reference to the embodiment of FIG. 1.

The X-drive housing 210 includes a pair of rails 220 (FIG. 14) that are used to support the arm bearing base 222. The arm bearing base 222 moves along the rails 220 on corresponding bearings 224. Journal bearings, ball bearings, or other suitable bearing structures can be utilized according to this invention to guide the bearing base 222. The bearing base 222 is driven by a lead screw 226 that rotates by operation of an X-drive motor 228 located at one end of the housing 210. The X-drive motor can directly drive the lead screw 226 or it can be interconnected with the lead screw 226 by gearing to attain the appropriate torque and speed desired to drive the arm along the X-axis. The bearing base 222 includes internal threading (not shown) that interengages the lead screw 226. Since the bearing base 222 is prevented from rotating about the X-axis by the rails 220, any rotation of the lead screw 226 is translated into linear motion of the bearing base along the screw axis and, hence, the arm 212.

The arm 212 is attached to the bearing base 222 by a shoulder yoke 230. The shoulder yoke 230 includes a recess 232 through which an additional lead screw 234 passes. This lead screw 234 is aligned along the Y-axis in a direction of extension of the arm 212.

Figure 10:
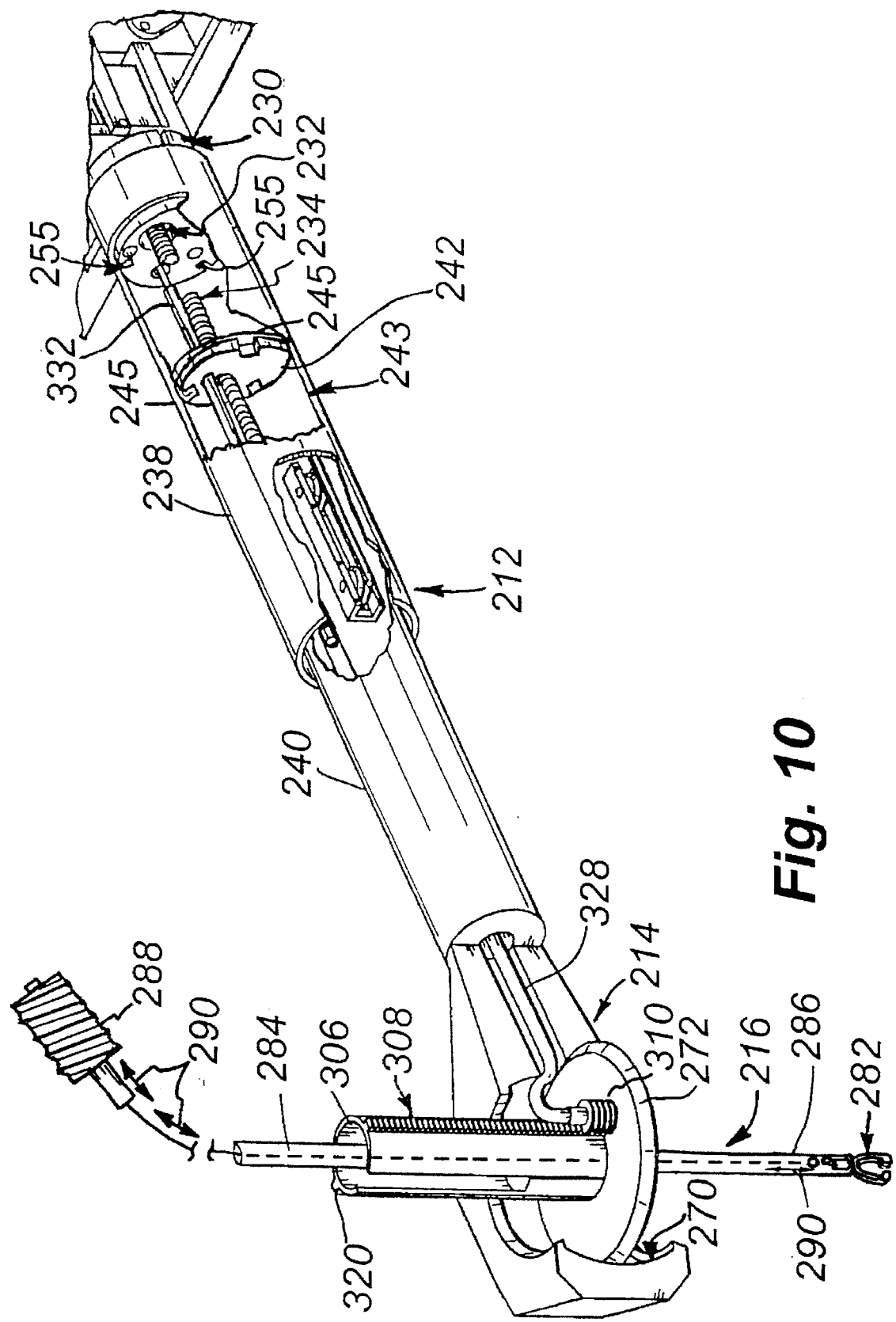
FIG. 10 is a more-detailed partially-exposed isometric view of the automated surgical instrument arm.

As detailed generally in FIGS. 9 and 10, the lead screw 234 passes between distal and proximal sections 238 and 240, respectively, of the arm assembly 212. The arm sections 238 and 240 have inside and outside diameters that enable the distal arm section 240 to telescope within the proximal arm section 238. The lead screw 234 is received by a threaded nut or plate 242 (FIG. 10) mounted within the distal arm section 240 at its proximal end 243. Thus, as the lead screw 234 rotates, the distal arm section 240 moves toward and away from the proximal arm section 238. A Y-drive motor 248 rotates to drive the Y-drive lead screw 234.

Figure 13:
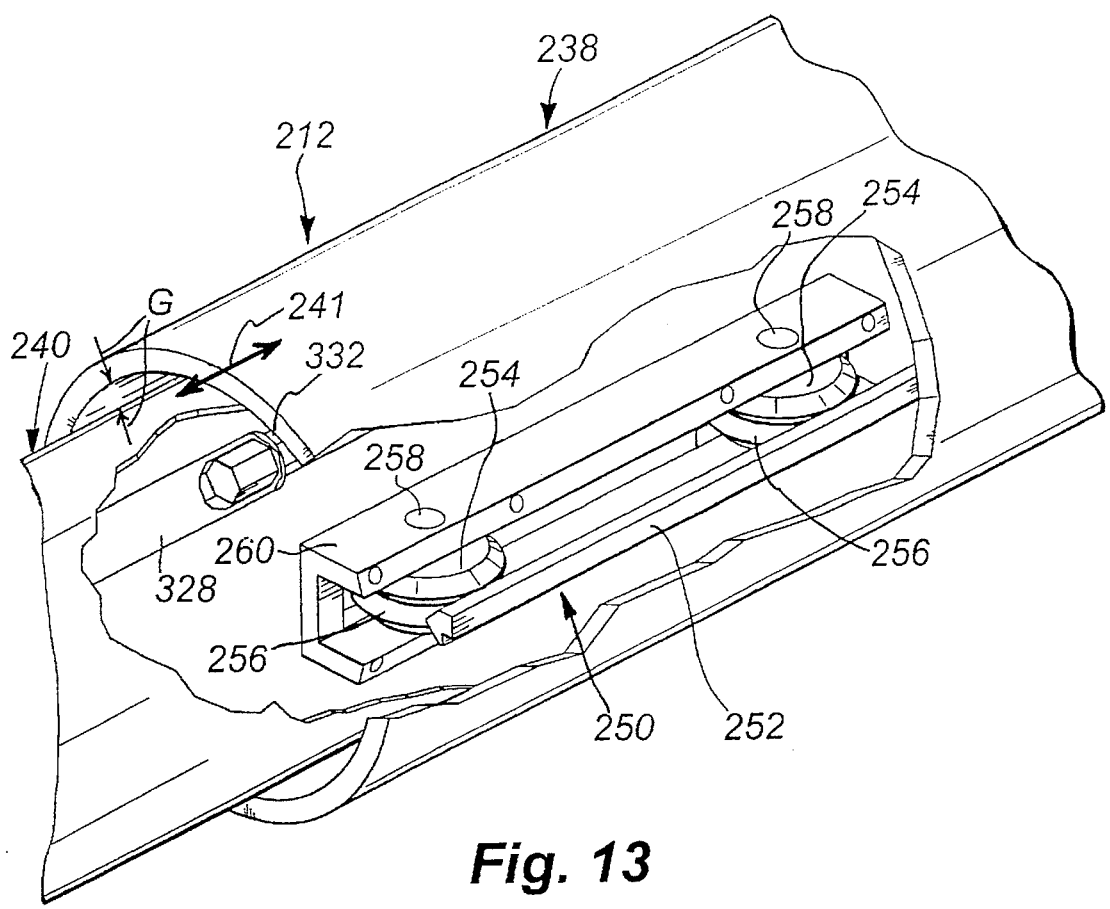
FIG. 13 is a more-detailed partially-exposed isometric view of the antirotation track of the arm.

As further detailed in FIG. 13, rotation between the distal and proximal arm sections 240 and 238, respectively, is prevented by a set of antirotation bearing assemblies 250. While it is contemplated that the distal arm section 240 and the proximal arm section 248 can engage each other such that the outer diameter of the distal section 240 is substantially flush with the inner diameter of the proximal section 238, it is preferred that the sections be spaced by a gap G. By providing a gap G improved sliding characteristics are obtained. Such sliding is facilitated by the antirotation bearing assemblies 250. Three such bearing assemblies are provided at 120° angles about the circumference of the arm 212. However, more or fewer bearing assemblies are contemplated.

The bearing assembly 250 particularly comprises a V-shaped rail 252 that is secured to the inner wall of the proximal arm section 238. A corresponding pair of rollers 254 project through gaps (not shown) in the wall of the distal arm section 240. These rollers 254 include V-shaped grooves 256 that are sized to engage the V-shaped rail 252. The rollers are mounted on axes 258 within a bearing channel structure 260 that is secured to the inner wall of the distal arm section 240. The nut or plate 242 described above can be mounted adjacent the bearing channel structure 260. Note that the plate 242 includes slots 245 that allow for clearance over the rails 252 as the plate 242 passes over the rails 252, during movement of the arm 212. The shoulder yoke 230 also includes slots 255 for the rails 252. It is contemplated that the rails can extend substantially the entire length of the proximal arm section 238 for added structural strength.

As noted above, the hand assembly 214 supports the laparoscopic instrument 216 according to this embodiment. The hand structure includes a hemispherical inner surface 270 (FIG. 12) that interengages a corresponding hemispherically-surfaced disk bearing 272. The hemispherical surface 270 is blocked on its upper and lower ends by shoulders 274 that project into the curve of the hemisphere. The hand 214 is open at its top and bottom by openings 276 and 278 to allow the instrument 216 to pass therethrough. The instrument 216 according to this embodiment is mounted within the approximate center of the disk 272.

Like the preceding embodiment, the instrument 216 can comprise laparoscope, trocar or any other mechanical surgical instrument, such as a scissor, grasper, pincer, electrocautery device, probe, syringe, vacuum retractor or laser scalpel suitable for laparoscopic surgery. As detailed in FIG. 10, the instrument at the distal end of the instrument 216 is a grasper 282 that is actuated by a linkage 284 passing through the lumen of the instrument's rigid (or semi-rigid) shaft 286. The linkage is interconnected with a remote linear motor 288 that can comprise a solenoid, feed screw or other suitable linkage-moving device. The motor 288 can be mounted adjacent the instrument 216 or at a point remote from the instrument adjacent, for example, the X-drive housing 210. If remotely positioned, the instrument 216 and motor 288 can be connected by, for example, a flexible shaft through which the linkage 284 moves the direction of the double arrow 290. The structure of the tool at the distal end of the shaft 286 should be adapted to suit the particular operative function for which the tool is necessary. The shaft end structure for a pair of exemplary tools are provided in FIGS. 5(a), 5(b), 6(a) and 6(b).

Figure 12:
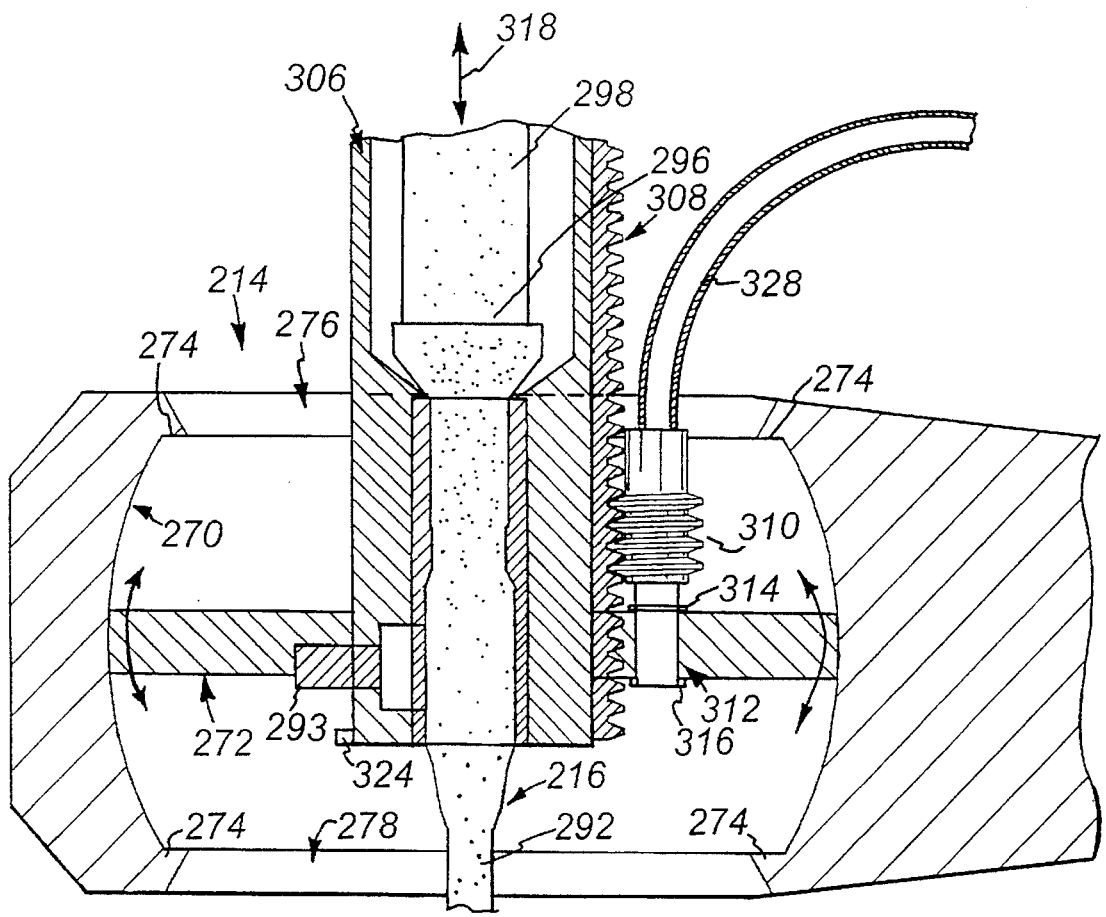
FIG. 12 is a cross section of the distal end of the arm taken along Line 12—12 of FIG. 11.

Similarly, as detailed in FIGS. 8, 9 and 12, the instrument 216 can comprise an optical channel 292 having an open distal end 294 for viewing the interior of a patient's body. A gas port 293 is provided along the channel 292 for infusion of gas into the patient as described in the preceding embodiment. The optical channel 292 can include a small fiberoptic viewing device as well as an illumination device (not shown). The opposing proximal end 296 of the instrument can be interconnected with a fiberoptic cable 298 that, in this embodiment, is fed to a remote camera 300 (FIG. 8). The camera can be located adjacent (above and, in-line-with, for example) the instrument 216 according to an alternate embodiment, or can be located at any remote point. Similarly, the camera can be replaced with an eye piece (not shown) that can be located at the end of a fiberoptic cable or atop the optical channel 292.

The remote camera 300, according to this embodiment, is interconnected with a monitor 302 of conventional design. The cable 298 should be sized so that it enables extension of the hand assembly 214 to a position that is at a maximum spacing from the remote camera 300 without causing kinking or buckling within the cable 298. The camera 300 can include a motor 303 that enables the camera to rotate the received image. The motor 303 can comprise a low-profile "pancake" motor or other suitable drive.

Figure 11:
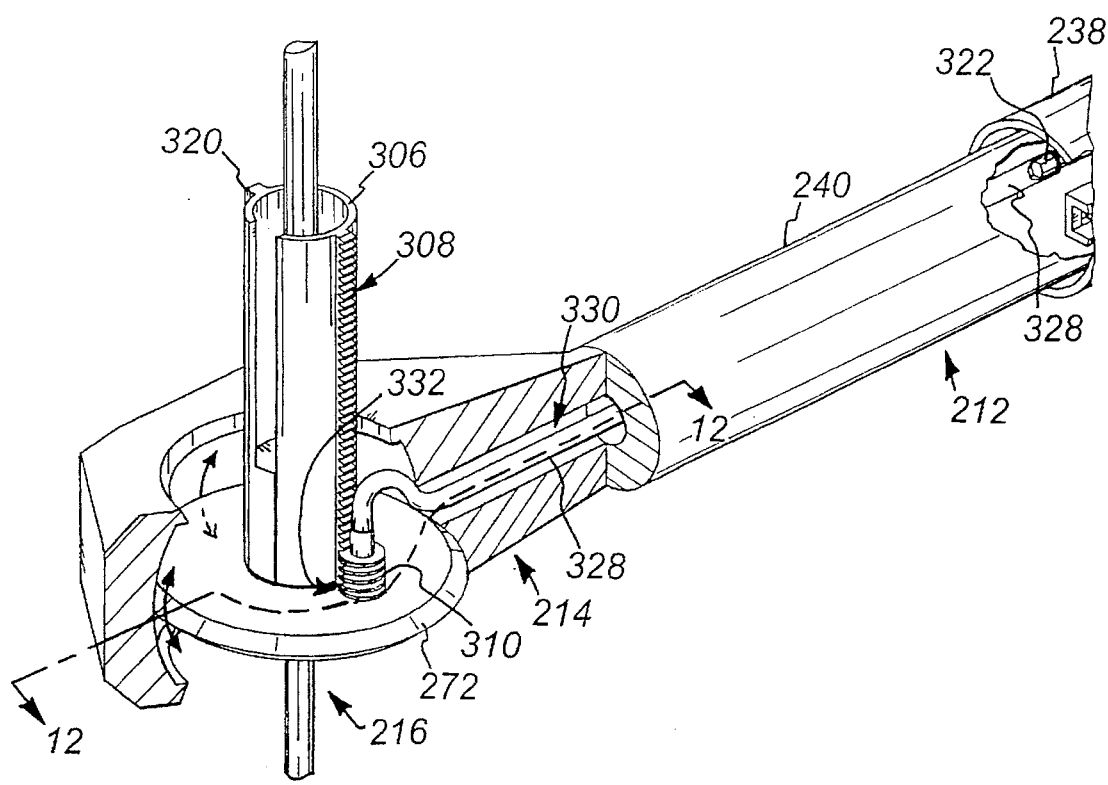
FIG. 11 is a more-detailed partially-exposed isometric view of the distal end of the arm.

With reference to FIGS. 11 and 12, the instrument 216 is seated within an outer housing 306 that includes a gear rack 308 is located along one side of the housing 306. The gear rack 308 interengages a worm gear 310 located in an orifice 312 on the disk 272 (FIG. 12) that provides a suitable rotational bearing surface. The gear should include collars 314 and 316 that prevent axial movement of the gear 310 relative to the disk 272. Rotation of the gear 312 causes the rack 308 to move upwardly and downwardly, thus, driving the instrument 216 and housing 306 along the Z-axis in the direction of the double arrow 318.

To prevent rotation of the housing 306 relative to the disk 272, a key 320 (FIGS. 8, 10 and 11) is located longitudinally along the housing 306 opposite the gear rack 308. A key way 322 (FIG. 11) is provided for the gear rack 308 and, likewise, an opposing key way (not shown) is provided for the key 320 in the disk 272. These key ways effectively prevent rotation of the instrument 216 and housing 306 about the Z-axis. The thickness of the disk 272 should also be sufficient to prevent pivotal misalignment of the housing 306 relative to the disk (e.g. "wobble") about the X-axis, Y-axis or a combination thereof.

The housing 306 can be provided with a stop 324 (FIG. 12) that prevents further upward movement of the housing beyond a predetermined limit. This stop can be mechanically or can comprise a limit switch interconnected with a controller that ceases further upward movement of the drive gear 310. A similar stop (not shown) can be provided to the upper end of the housing 306. The length of the housing can vary depending upon the particular application for the instrument 216. Some instruments may require a relatively short and precise movement distance, while others may require a substantial movement distance to reach their desired location and/or focal length. Thus, housing lengths can vary accordingly.

Figure 14:
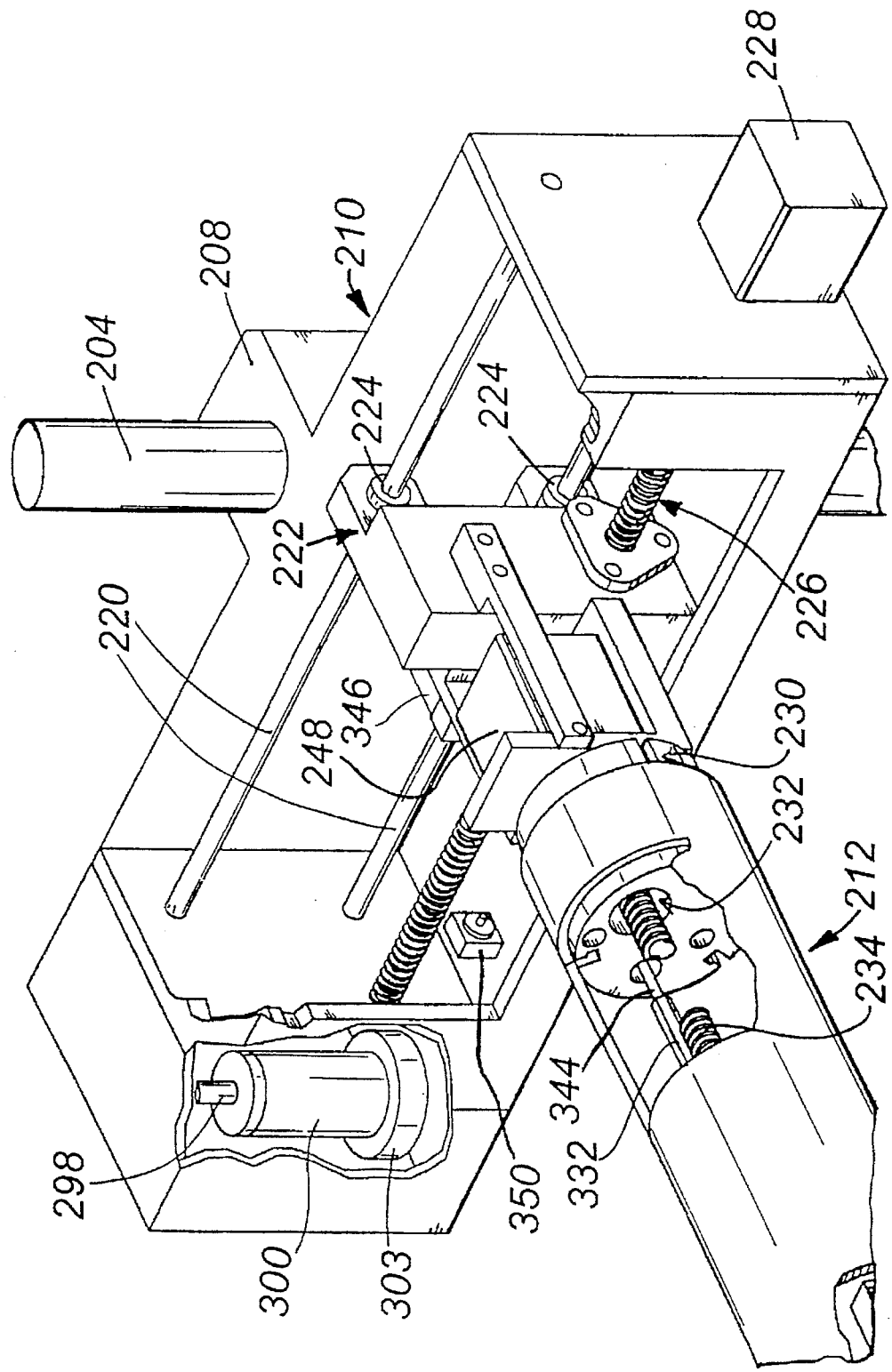
FIG. 14 is a more-detailed partially-exposed isometric view of the X-drive housing and arm base.

With further reference to the drive gear 310, a flexible shaft 328 delivers rotational movement to the gear 310. The flexible shaft extends from the hand assembly 214 and returns into an orifice 330 (FIG. 11) within the hand assembly 214 and the distal arm section 240. The shaft 328 extends proximally to engage a hexagonal drive shaft 332 (FIGS. 9, 11, 13 and 14). The inner wall of the drive shaft 328 is adapted, at its proximal end, to engage the hexagonal drive shaft 332 and to slide relative to the drive shaft as the distal arm section 240 is moved toward and away (double arrow 241, FIG. 13) from the proximal arm section 238. Note that a bearing 340 (FIG. 9) is provided at the junction of the distal arm section 240 with the hand assembly 214 to enable free rotation of the flexible shaft. The bearing 340 also substantially retains the shaft from movement along the Y-axis so that the shaft 328 slides relative to the hexagonal drive shaft 332. The hexagonal drive shaft 332 is interconnected by a proximal drive shaft 344 (FIG. 14) to a Z-drive motor 346 (FIG. 14).

With reference again to FIGS. 11 and 12, the hemispherical surface 270 of the hand assembly 214 interacts with the corresponding hemispherical edge of the disk 272 to enable the instrument 216 to freely swivel within a predetermined range of movement (approximately +/−20°–30° in this embodiment) in the manner of a "ball-and-socket" joint.

Other swivel mechanisms that enable pivoting along at least two orthogonal axes, such as a gimbal structure, are also desirable. Pivoting along only one axis is also contemplated. However, maximum pivoting freedom is preferred for ease of manipulation.

It is contemplated that, in operation, the instrument 216 is first directed through an incision (not shown) in the patient's body, by manual lowering and use of the Z-drive motor, and then can be manipulated to reach a predetermined location in the body by rotating the X-drive and Y-drive motors 228 and 248, respectively, to cause the instrument to pivot about the incision. The flexible shaft 328 flexes in response to the swiveling of the disk 272 relative to the hemispherical surface 270 to enable relatively resistance-free swiveling of the instrument 216. In this manner, the X, Y, and Z-drive motors can be powered to move the distal end of the instrument 216 about the body, through an incision therein, within a predetermined range.

Each of the drives can be provided with limit switches such as the X-drive limit switch 350 (FIGS. 9 and 14) utilized for the X-drive. Each drive can include absolute limit switches such as the X-drive limit switch 350, which prevent mechanical damage to the unit by ceasing operation of the drive motor when a particular component reaches it outward maximum travel distance. Similarly, as described above, each component can include appropriate strain gauges or other force sensors such as the strain gauge 352 (FIG. 8) that monitor the force generated on the components by interaction with the patient's body. Such strain gauges can be calibrated to ensure that the force bearing upon the body by the instrument 216 does not exceed a predetermined maximum. Such maximum can be dependent on the force that would cause internal damage to the patient.

The limit switches, drive motors and strain gauges according to this embodiment can each be interconnected with a controller 354 (FIG. 8) that can include a microprocessor or microcomputer interface. The controller provides outputs, based upon movement signals input by the operator. The controller 354 can include a display screen 356 that indicates movements undertaken by the device, forces exerted on the device, and other relevant data. The controller 354 is interconnected with a joystick or similar manual interface that translates the operator's inputs into movement of each of the drive motors. A foot pedal 360 can also be provided to operate the Z-axis drive motor 346 or to actuate a tool at the distal end of the shaft 286 (FIG. 10). Each of the motors 228, 248 and 346 used herein can comprise a stepper motor or servomotor. The motors can be geared to provide relatively slow movement and high torque. The motors can include internal force sensors that act as travel limiters to protect the patient. All information, according to this embodiment, is routed to and from the controller 354 to enable effective movement of the instrument 216 within the body cavity of the patient.

As illustrated generally in FIG. 9, the hand can also include a sleeve 370 that joins the hand assembly 214 to the distal arm section 240. The sleeve can include a quick disconnect lock (not shown) that enables the hand to be rapidly removed from the arm 212. The flexible shaft 328 can be similarly connected at the junction between the hand 214 and the distal arm section 240 so that, in an emergency, the laparoscopic instrument section can be disconnected from the arm for quick removal or reorientation.

The materials utilized to construct the instrument 200 according to this invention should be compatible with those normally present in an operating room environment. They should be easily sterilizable, resistant to staining and have relatively low friction coefficients. It is contemplated that the arm 212 can be manufactured from a composite material such as carbon fiber, a metal such as stainless steel or a plastic such as Delrin®. The arm should be lightweight and rigid. The hand assembly 214 can, likewise, be constructed from a composite or plastic. The hemispherical surface 270 and the disk 272 should be constructed from a low friction material such as Delrin® plastic or a combination of plastic and highly-polished stainless steel. The instrument 216 can be constructed of a combination of stainless steel and plastic or other suitable materials. Similarly, the feed screws can be constructed of stainless steel or plastic. Sealed ball bearings or slide bearings can be utilized where appropriate to support the shafts. The X-drive housing 210 can comprise a plastic, composite or metal casing.

The instrument 216 can be mounted within the housing 306 permanently or, alternatively, can be removably seated in the housing 306. The instrument can be locked in place by a spring loaded quick-disconnect mechanism (not shown). While a joystick 358 and food pedal 360 are shown as control mechanisms, it is also contemplated that control of the X, Y and Z-drives can occur by means of an eye tracking mechanism that would utilize an eye piece to track the location of the surgeon's eye and, hence, position the distal end of the instrument 216 at the viewed location. Similarly, the components of the instrument 200 can include force sensors that respond to slight pressures exerted by the operator in a predetermined direction on the instrument 216. Such sensors can comprise strain gauges or other suitable force sensors (such as the strain gauge 352 (FIG. 8) or a grid-force sensor, which could be located in a sleeve (not shown) around the cannula-available, for example, from Tekscan Company of Boston, Mass.) located along the body of the instrument 200 at appropriate locations. The force sensors, upon sensing a force in a predetermined direction would transmit force data to the controller which, in turn, would transmit a corresponding movement signal back to the device as long as the force is imparted to the particular portion of the instrument 200. Once the force is removed, the instrument comes to rest at its new location. Such force sensors can be incorporated into the X, Y and Z-drive motors. A computer interface (such as a trackball 375 of FIG. 8) can be located near or on the instrument to enable the operator to manipulate data while operating the instrument.

Control can also be facilitated by a voice recognition unit interconnected with a microcomputer. The voice recognition unit can be trained to learn simple commands such as "IN", "OUT", "LEFT", "RIGHT", "MOVE", "X° FOR Y DISTANCE". The controller would correlate such commands to predetermined movement directions and distances over the allowed range of movement for the instrument.

Any of the control mechanisms described above can be equipped with a memory function that stores locations upon command and enables the operator to reposition the distal end of the instrument at a previous position and orientation subsequent to further movement. Storing of positions would occur when a desired position has been attained. At such time, a "STORE" command is input to the controller 354.

Additionally, while the illustrated embodiment shows optical cables and control linkages exiting from the instrument 216 at a location remote from the arm 212, it is contemplated that the arm can comprise a series of lumens to carry various data, gas and mechanical interconnections so that the instrument is connected directly to the instrument shaft.

Similarly, while feed screw drives are utilized for the X-axis and Y-axis drives and a rack and worm gear drive is utilized for the Z-axis drive, it is contemplated that the Z-axis drive can comprise a feed screw similar to that described in the preceding embodiment that would be mounted upon the disk 272 or another form of linear drive suitable for mounting relative to the hand assembly 214. Similarly, the X-axis drive and Y-axis drive can comprise alternate linear drive mechanisms such as rack and pinion systems.

The foregoing has been a detailed description of a preferred embodiment. Various modifications and equivalents can be made without departing from the spirit and scope of this invention. This description is, therefore, meant to be taken only by way of example and not to otherwise limit the scope of the invention.

What is claimed is:

1. An automated surgical instrument comprising:
   surgical tool;
   a rigid cannula constructed and arranged for insertion through an incision in a body of a patient, the cannula having a lumen that receives the surgical tool therein and the cannula being elongated along a first direction;
   a drive for moving the cannula along the first direction;
   an arm having a proximal end and a distal end, the cannula being supported at the distal end, the arm having a second drive to move the cannula along a second direction transverse to the first direction;
   an arm support located adjacent the proximal end of the arm and a third drive that moves the cannula in a third direction that is transverse to each of the first direction and the second direction; and
   a swivel assembly having a swivel base mounted at the distal end of the arm and having a pivot member that rotates relative to the swivel base along at least one pivot axis that is aligned with at least one of the second direction and the third direction whereby the cannula pivots about the axis.

2. The automated surgical instrument as set forth in claim 1 wherein the first drive comprises a gear rack located adjacent the cannula and a gear that moves the rack in the first direction.

3. The automated surgical instrument as set forth in claim 2 wherein the swivel assembly comprises a hemispherical socket and an interengaging hemispherical support, the cannula being located within the support and the gear being mounted on the support.

4. The automated surgical instrument as set forth in claim 3 wherein the gear comprises a worm gear and further comprising a flexible shaft interconnected with the worm gear at a first end, the flexible shaft having a second end, remote from the first end, interconnected with a first drive motor.

5. The automated surgical instrument as set forth in claim 4 wherein the first drive motor is located adjacent the proximal end of the arm.

6. The automated surgical instrument as set forth in claim 1 wherein the arm comprises a pair of arm sections that move relative to each other.

7. The automated surgical instrument as set forth in claim 6 wherein the arm sections comprise telescoping sections and wherein the second drive comprises a linear drive that moves one of the telescoping sections relative to the other of the telescoping sections along the second direction.

8. The automated surgical instrument as set forth in claim 7 wherein the linear drive comprises a lead screw rotated by a second drive motor.

9. The automated surgical instrument as set forth in claim 1 wherein the proximal end of the arm includes a bearing base that enables movement of the proximal end in the third direction on a bearing surface.

10. The automated surgical instrument as set forth in claim 9 wherein the bearing surface comprises a rod structure oriented along the third direction.

11. The automated surgical instrument as set forth in claim 10 further comprising a base that houses the rod structure, the base further comprising a lead screw that drives the bearing base along the third direction, the lead screw being driven by a third drive motor.

12. The automated surgical instrument as set forth in claim 11 wherein the base includes a mounting member constructed and arranged to enable the base to be fixedly-mounted in a predetermined spatial relationship relative to a patient.

13. The automated surgical instrument as set forth in claim 1 further comprising a mounting base interconnected to the proximal end of the arm, the mounting base being constructed and arranged to enable mounting of the arm in a predetermined spatial relationship relative to the patient.

14. The automated surgical instrument as set forth in claim 13 further comprising an upright support interengaged with the mounting base, the mounting base being locatable at a predetermined location on the upright support.

15. The automated surgical instrument as set forth in claim 14 wherein the upright support includes a base clamp for mounting the upright support to an operating table.

16. The automated surgical instrument as set forth in claim 1 further comprising the at least one limit switch that deactivates at least one of the first drive, the second drive and the third drive, when a predetermined maximum distance of travel is attained by at least one of the first drive, the second drive and the third drive.

17. The automated surgical instrument as set forth in claim 1 further comprising at least one limit switch, the limit switch being constructed and arranged to signal a predetermined maximum force exerted by the instrument on the patient.

18. The automated surgical instrument as set forth in claim 17 further comprising a controller that disables driving of at least one of the first drive, the second drive and the third drive in response to receipt of a signal by the at least one limit switch.

19. The automated surgical instrument as set forth in claim 1 wherein the cannula includes an optical channel for a laparoscope.

20. The automated surgical instrument as set forth in claim 19 further comprising an optical cable interconnecting the optical channel to a camera remote from the cannula.

21. The automated surgical instrument as set forth in claim 1 wherein the cannula includes a linkage disposed within a lumen of the cannula, the linkage moving to operate a surgical tool located at the distal end of the cannula.

22. The automated surgical instrument as set forth in claim 21 further comprising a motor for moving the linkage located proximally of the distal end of the cannula.

23. The automated surgical instrument as set forth in claim 22 wherein the motor is located remote from the cannula.

24. The automated surgical instrument as set forth in claim 1 further comprising a controller that controls each of the first drive, the second drive and the third drive, the controller including a manual switch, interconnected thereto, for manipulating each of the first drive, the second drive and the third drive.

25. The automated surgical instrument as set forth in claim 24 wherein the manual switch comprises a joystick controller.

26. The automated surgical instrument as set forth in claim 24 wherein the manual switch includes a foot pedal.

27. The automated surgical instrument as set forth in claim 24 further comprising a sensor system constructed and arranged so that application of pressure to the instrument causes at least one of the first drive, the second drive and the third drive to move in response to and in a direction of the application of pressure thereto.

28. The automated surgical instrument as set forth in claim 1 wherein the cannula includes an optical channel having a camera optically interconnected thereto.

29. The automated surgical instrument as set forth in claim 28 wherein the camera is rotatable relative to the optical channel to change a rotational orientation of an image transmitted by the camera.

30. The automated surgical instrument as set forth in claim 29 wherein the camera includes a rotary drive motor to rotate the camera relative to the optical channel.

31. The automated surgical instrument as set forth in claim 1 further comprising a sensor system that records a predetermined spatial orientation of the cannula at a first time and a controller that controls at least one of the first drive, the second drive and the third drive to move the cannula to the predetermined spatial orientation at a second time.

32. An automated surgical instrument comprising:

a surgical tool;

a rigid elongated cannula having a lumen for receiving the surgical tool;

an arm that supports the cannula in a predetermined spatial orientation, the arm having a distal end that receives the cannula and a proximal end remote from the cannula;

an arm base that supports the arm, the base being interconnected with the proximal end of the arm:

a drive mechanism operatively connected to the arm to move the arm in at least a first direction toward and away from the arm base to, thereby, move the cannula toward and away from the arm base; and a pivot mechanism located at the distal end of the arm, the pivot mechanism including a pivot base mounted on the distal end of the arm and a cooperating pivot member operatively interconnected with the cannula, the pivot member mounted to the pivot base moving relative to the pivot base along at least a first axis in response to a moment applied to the cannula based upon movement of the arm in the first direction.

33. The automated surgical instrument as set forth in claim 32 wherein the drive mechanism is constructed and arranged to move the arm in a second direction to, thereby, move the cannula, and wherein the pivot is constructed and arranged to enable the cannula to pivot relative to the arm in response to movement of the arm in the second direction.

34. The automated surgical instrument as set forth in claim 32 wherein the drive mechanism is constructed and arranged to move the cannula substantially in a direction of elongation of the cannula.

35. The automated surgical instrument as set forth in claim 32 wherein the pivot mechanism comprises a pair of slidably interengaging hemispherical surfaces.

* * * * *